US012630719B2

(12) United States Patent
Arsenjans et al.

(10) Patent No.: US 12,630,719 B2
(45) Date of Patent: May 19, 2026

(54) FLUORESCENT ACRIDINIUM SALTS, SYNTHESIS THEREOF AND USE FOR DETECTION OF CARDIOLIPIN

(71) Applicant: LATVIAN INSTITUTE OF ORGANIC SYNTHESIS, Riga (LV)

(72) Inventors: Pavels Arsenjans, Riga (LV); Pavels Dimitrijevs, Daugavpils (LV)

(73) Assignee: Latvian Institute of Organic Synthesis, Riga (LV)

( * ) Notice: Subject to any disclaimer, the term of this patent is extended or adjusted under 35 U.S.C. 154(b) by 635 days.

(21) Appl. No.: 17/777,506

(22) PCT Filed: Sep. 11, 2020

(86) PCT No.: PCT/IB2020/058457
§ 371 (c)(1),
(2) Date: May 17, 2022

(87) PCT Pub. No.: WO2021/105780
PCT Pub. Date: Jun. 3, 2021

(65) Prior Publication Data
US 2023/0013542 A1 Jan. 19, 2023

(30) Foreign Application Priority Data
Nov. 28, 2019 (LV) ........................................ P-19-64

(51) Int. Cl.
*C09B 69/00* (2006.01)
*G01N 33/58* (2006.01)
*G01N 33/92* (2006.01)

(52) U.S. Cl.
CPC ......... *C09B 69/008* (2013.01); *G01N 33/582* (2013.01); *G01N 33/92* (2013.01)

(58) Field of Classification Search
CPC .............................. C09B 69/008; G01N 33/92
See application file for complete search history.

(56) References Cited

U.S. PATENT DOCUMENTS 4,193,983 A 3/1980 Ullman et al.

FOREIGN PATENT DOCUMENTS

| | | | |
|---|---|---|---|
| CN | 107090190 | A | 8/2017 |
| CN | 107807238 | A | 3/2018 |
| WO | WO 2013/093481 | A1 | 6/2013 |
| WO | WO 2015/153813 | A1 | 10/2015 |
| WO | WO 2021105780 | | 6/2021 |
| WO | WO 2022038424 | | 2/2022 |

OTHER PUBLICATIONS

No new references cited by the Examiner.*
Kaewsuya P et al., "Fluorescent determination of cardiolipin using 10-N-nonyl acridine orange", Analytical and Bioanalytical Chemistry, Springer, Berlin, DE, vol. 387, No. 8, Feb. 15, 2007, pp. 2775-2782.
Kaewuya P et al., "Comparison of N-alkyl acridine orange dyes as fluorescence probes for the determination of cardiolipin", Analytica Chimica Acta, Elsevier, Amsterdam, NL, vol. 626, No. 2, Sep. 26, 2008, pp. 111-118.
International Search Report for PCT/IB3030/058457, mailed on Sep. 12, 2020, 2 pages.
International Search Report and Written Opinion in International Appln No. PCT/IB2020/058457, mailed on Dec. 9, 2020, 8 pages.
Mather et al., "Polycations induce the release of soluble intermembrane mitochondrial proteins," Biochem Biophys Acta, Sep. 2000, 1503(3):357-368.
Nicolay et al., "The Interaction of Adriamycin with Cardiolipin in Model and Rat Liver Mitochondrial Membranes," Biochem Biophys Acta, Jun. 1984, 778(2):359-371.
Parker et al., "Nuclear magnetic resonance study of doxorubicin binding to cardiolipin containing magnetically oriented phospholipid bilayers," Biochem Biophys Acta, Jun. 2001, 1514(2):206-216.
Sautrey et al., "Negatively-charged Lipids as Potential Target for New Amphiphilic Aminoglycoside Antibiotics: a biophysical study," J. Biological Chem., May 2016, M115.665364, 35 pages.
Sinibaldi et al., "Insights into Cytochrome c-Cardiolipin Interaction. Role Played by Ionic Strength," Biochemistry, Apr. 2008, 47(26):6928-6935.
Soussi et al., "H-n.m.r. evaluation of the ferricytochrome c-cardiolipin interaction," Biochem. J., Aug. 1989, 265(1):227-232.

* cited by examiner

*Primary Examiner* — Shawquia Jackson
(74) *Attorney, Agent, or Firm* — Fish & Richardson P.C.

(57) ABSTRACT

The present invention relates to a novel substituted acridinium salts as fluorescent dyes, as well as methods of their manufacturing and use of the disclosed compounds for the detection of cardiolipin.

11 Claims, 1 Drawing Sheet

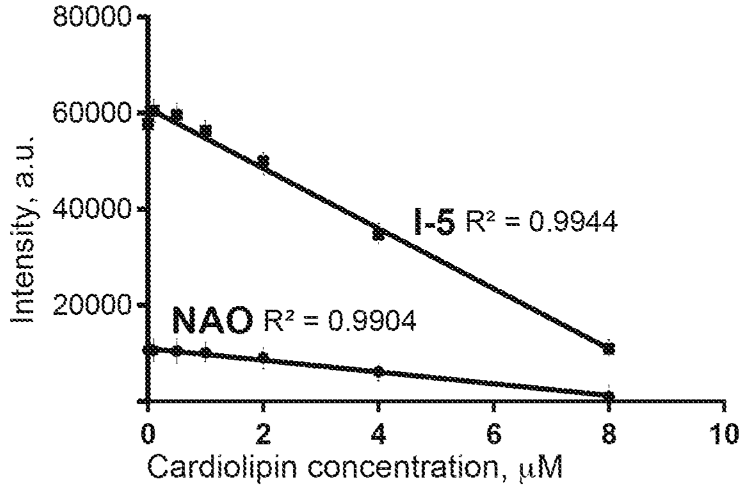
80000
60000
40000
20000
Intensity, a.u.
I-5 R² = 0.9944
NAO R² = 0.9904
0
2
4
6
8
10
Cardiolipin concentration, μM

FLUORESCENT ACRIDINIUM SALTS, SYNTHESIS THEREOF AND USE FOR DETECTION OF CARDIOLIPIN

CROSS REFERENCE TO RELATED APPLICATIONS

This application is a U.S. national phase filing under 35 U.S.C. § 371 of International Application No. PCT/IB2020/058457, filed Sep. 11, 2020, which claims priority to Latvian Application No. P-19-64, filed Nov. 28, 2019. The International Application was published in English on Jun. 3, 2021 as WO 2021/105780 under PCT Article 21(2). The contents of the prior applications are incorporated herein by reference in their entirety.

FIELD OF THE INVENTION

The present invention relates to a novel fluorescent compounds, synthesis thereof, and methods of using same. The present invention discloses novel 3,6-di(azetidin-1-yl)-10-substituted-acridin-10-ium salts, a process of the manufacture and the use of the disclosed compounds for detection of cardiolipin.

BACKGROUND OF THE INVENTION

Mitochondria are vital organelles that are involved in a large array of metabolic and bioenergetic processes needed for cell survival. Phospholipids are the main building blocks of all the membranes, and every organelle's membrane bears its unique phospholipid composition.

Cardiolipin (CL) is a unique phospholipid which is localized and synthesized in the inner mitochondrial membrane (IMM) where it constitutes approximately 20% of total IMM phospholipids. It is now widely accepted that CL plays an important role in mitochondrial membrane morphology, stability, dynamics and is required for optimal activity of several mitochondrial membrane proteins (e.g. electron transport chain (ETC) complexes, cytochrome C). [1] Cardiolipin peroxidation due to increased reactive oxygen species (ROS) production leads to decreased activity of ETC complex I, III and IV and promotes cytochrome C release from mitochondria which in turn induces apoptosis by caspase cascade activation. [2]

In addition to its important role in the apoptosis pathway, the level of CL is also of clinical significance. The depletion of CL is a major indicator of aging, Barth syndrome, and a number of diseases associated with mitochondrial respiratory function such as heart ischemia, cardiac failure, diabetes and neurodegenerative disorders. [3-6] Therefore, it is highly important to develop an effective method for the detection and quantification of CL.

Besides mitochondrial membrane, CL is the characteristic lipid of bacterial membranes with CL content varying between different bacterial strain. [7] Owing to its certain localization (either mitochondrial inner membrane or bacterial membrane) and peculiar functions, cardiolipin has driven scientists' attention as a target molecule for mitochondria function protecting drugs as well as a target for antibacterial agents. [8,9]

In addition, some drugs side effects can be explained by their interaction with CL, for example, vancomycin's nephrotoxicity or cardiotoxicity of chemotherapy drugs. [10,11]

In the early 1980s a fluorescent dye, 10-N-nonyl acridine orange, was introduced for selective CL detection and mitochondria staining. [12]

In the presence of CL, the green fluorescence of NAO is decreased allowing to quantitatively analyze CL content ranging from 0.2 to 10 μM. [13] However, NAO suffers from poor solubility in physiological media, low PLQY (photoluminescence quantum yield, Φ), as well as small intensity differences between CL-bound and unbound states.

Therefore, an improvement in solubility in physiological media, increase of PLQY, fluorescence brightness and photostability are among the main tasks in development of new effective fluorescent dyes for cell organelle imaging.

THE PRESENT INVENTION

We have surprisingly determined that certain 3,6-di(azetidin-1-yl)-10-substituted-acridin-10-ium salts exhibit superior PLQY than NAO (nonyl acridine orange) and therefore may act as efficient fluorescent dyes for the detection of cardiolipin. These substances may be administered in the form of a composition, wherein they are present together with one or more acceptable diluents, carriers, or excipients.

Objects of the Invention

It is an object of the present invention to provide novel fluorescent compounds, useful for detection of cardiolipin and methods for manufacturing of disclosed compounds.

SUMMARY OF THE INVENTION

We disclosed compounds selected from those of Formula I

I

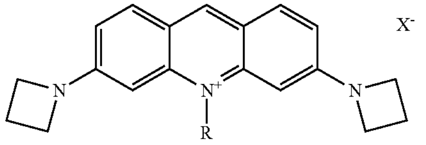

R represents $C_{1-15}$ alkyl; $C_{1-3}$ deuterated alkyl, $C_{1-6}$-alkylene-silyl($C_{1-3}$-alkyl)$_3$ $X^-$ represents chloride, bromide, iodide;

As used herein, the term "alkyl" refers to a straight or branched hydrocarbon chain, containing the indicated number of carbon atoms. For example, $C_1$-$C_6$ alkyl indicates that the alkyl group may have from 1 to 6 (inclusive) carbon atoms. The term "alkylene" refers to a divalent alkyl, e.g., $-CH_2-$, $-CH_2CH_2-$, $-CH_2CH_2CH_2-$, $-CH_2CH(CH_3)CH_2-$. An alkyl or alkylene may be optionally substituted. Alkyl group may contain deuterium.

Specific compounds of Formula I within the present invention include but are not limited to:

3,6-di(azetidin-1-yl)-10-methylacridin-10-ium iodide;

3,6-di(azetidin-1-yl)-10-(methyl-$d_3$)acridin-10-ium iodide;

3,6-di(azetidin-1-yl)-10-nonylacridin-10-ium iodide;

3,6-di(azetidin-1-yl)-10-dodecylacridin-10-ium iodide;

3,6-di(azetidin-1-yl)-10-(3-(trimethylsilyl)propyl) acridin-10-ium iodide.

BRIEF DESCRIPTION OF DRAWINGS

FIG. 1 depicts linear regression curves for NAO and I-5 titration with cardiolipin.

DETAILED DESCRIPTION OF THE INVENTION

Searching for fluorescent compounds to be used for the determination of cardiolipin we unexpectedly discovered that 3,6-di(azetidin-1-yl)-10-substituted-acridin-10-ium salts of Formula I exhibit superior PLQY compared to NAO. Our finding is astonishing, because it is well known, that NAO is widely used dye for the detection of cardiolipin. We discovered that high quantum yield is typical for a number of compounds in series of 3,6-di(azetidin-1-yl)-10-substituted-acridin-10-ium salts, especially if there is silyl group present in alkyl chain, $CH_3$ or $CD_3$ in position 10 of this scaffold.

Scheme 1 describes the preparation of compounds of Formula I of the present invention. All of the final compounds of the present invention can be prepared by procedures described in these charts or by procedures analogous thereto, which procedures would be well known to one of ordinary skill in organic chemistry. All of the variables used in the scheme are as defined below or as in the claims.

General Procedure of Compounds Preparation of Formula I (Scheme 1)

Quaternization of acridines is a challenging task. All trusted reports in literature confirm requiring of elevated temperature, excess of alkylating agent and prolonged heating. It results in the formation of difficult separable crude mixtures due to diamino acridines are sensitive to prolonged heating. In our hands quaternization of 1 proceeded even slower than the same reaction with acridine orange. Surprisingly, we have found that the treatment of 1 with alkyl halides in the presence of inorganic salts (e.g. phosphates, carbonates) led to the fast completion of the reaction. Notably, reaction time was reduced from 2-3 days to less than 1 hour. Moreover, much smaller number of by-products has been detected making isolation of I easier.

Scheme 1. General procedure toward compounds of Formula I.

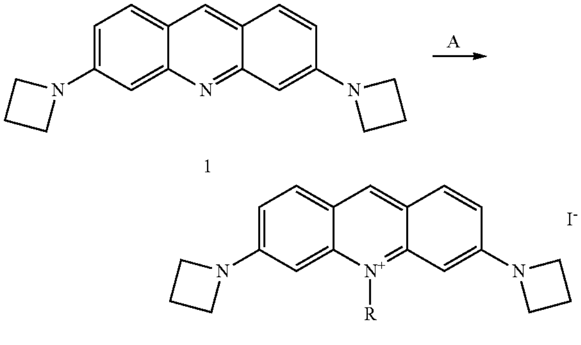

1

I-1-I-5

Reaction conditions: A-alkyl halide; $K_3PO_4$; toluene or dichlorobenzene, 100-170° C., 10-40 min.

EXAMPLES

Preparation of the disclosed compounds of the present invention is described in the following examples, which are intended as an illustration of and not a limitation upon the scope of the invention.

Example 1

3,6-di(azetidin-1-yl)-10-methylacridin-10-ium iodide (I-1)

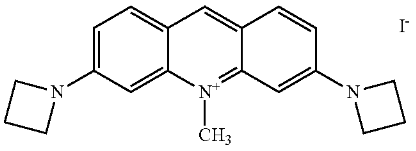

To a preheated suspension of 1 (25 mg, 0.086 mmol) in 4 ml of toluene at 100° C. potassium phosphate (42 mg, 0.2 mmol) was added followed by the addition of iodomethane (0.5 ml). Resulting mixture was stirred under reflux for 40 min. Then reaction mixture was filtered through aluminum oxide pad and washed with 30 ml of $CH_2Cl_2/CH_3OH$ (50:1) mixture. Volatiles were evaporated to yield 28 mg of I-1 as red solid (75%).

$^1H$ NMR (400 MHz, Methanol-$d_4$/$CDCl_3$) δ 8.34 (s, 1H), 7.67 (d, 2H), 6.59 (dd, 2H), 6.17 (d, 2H), 4.20 (t, 8H), 3.98 (s, 3H), 2.55-2.44 (m, 4H). $^{13}C$ NMR (101 MHz, Methanol-$d_4$/$CDCl_3$) δ 155.3, 143.7, 143.0, 133.3, 117.1, 112.5, 90.7, 51.6, 36.3, 16.0. HRMS (ESI): calcd. for $C_{20}H_{22}N_3^+$ [M]$^+$ calcd. 304.1808, found 304.1823.

Example 2

3,6-di(azetidin-1-yl)-10-(methyl-$d_3$)acridin-10-ium iodide (I-2)

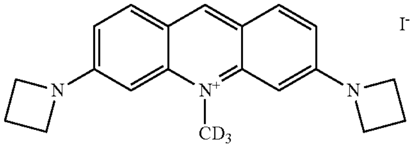 [SMILES: [2H]C([2H])([2H])[n+]1c2cc(N3CCC3)ccc2cc2ccc(N3CCC3)cc21 ; [I-]]

To a preheated suspension of 1 (25 mg, 0.086 mmol) in 4 ml of toluene at 100° C. potassium phosphate (42 mg, 0.2 mmol) was added followed by the addition of iodomethane-$d_3$ (0.3 ml). Resulting mixture was stirred under reflux for 15 min. Then reaction mixture was filtered through aluminum oxide pad and washed with 30 ml of $CH_2Cl_2/CH_3OH$ (50:1) mixture. Volatiles were evaporated to yield 23 mg of 1-2 as red solid (62%).

$^1H$ NMR (400 MHz, $CDCl_3$) δ 8.31 (s, 1H), 7.63 (d, 2H), 6.57 (dd, 2H), 6.11 (dd, 2H), 4.23-4.10 (m, 8H), 2.55-2.44 (m, 4H). HRMS (ESI): calcd. for $C_{20}H_{19}D_3N_3^+$ [M]$^+$ calcd. 307.2002, found 307.2005.

Example 3

3,6-di(azetidin-1-yl)-10-nonylacridin-10-ium iodide (I-3)

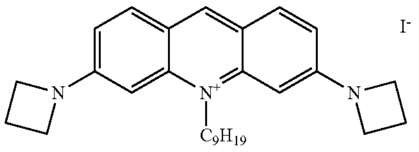

To a preheated suspension of 1 (25 mg, 0.086 mmol) in 4 ml of dichlorobenzene at 170° C. potassium phosphate (42 mg, 0.2 mmol) was added followed by the addition of 1-iodononane (0.5 ml). Resulting mixture was stirred under reflux for 45 min. Then reaction mixture was evaporated, and residue was purified by flash chromatography on aluminum oxide using mixture of $CH_2Cl_2/C_2H_5OH$ (10:1) as eluent to yield 36 mg of 1-3 (76%).

$^1$H NMR (400 MHz, Chloroform-d) δ 8.58 (s, 1H), 7.83 (d, 2H), 6.68 (dd, 2H), 6.17 (d, 2H), 4.55 (t, 2H), 4.28 (t, 8H), 2.64-2.56 (m, 4H), 1.94-1.90 (m, 2H), 1.62-1.55 (m, 2H), 1.38-1.16 (m, 10H), 0.85 (t, 3H). HRMS (ESI): calcd. for $C_{28}H_{38}N_3^+$ $[M]^+$ calcd. 416.3060, found 416.3058.

Example 4

3,6-di(azetidin-1-yl)-10-dodecylacridin-10-ium iodide (I-4)

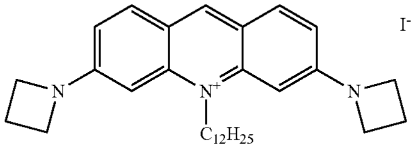

To a preheated suspension of 1 (25 mg, 0.086 mmol) in 4 ml of dichlorobenzene at 170° C. potassium phosphate (42 mg, 0.2 mmol) was added followed by the addition of 1-iodododecane (0.5 ml). Resulting mixture was stirred at 170° C. for 10 min. Then reaction mixture was filtered through aluminum oxide pad to yield 27 mg of I-4 (54%).

$^1$H NMR (400 MHz, Acetonitrile-$d_3$) δ 8.43 (s, 1H), 7.72 (d, 2H), 6.68 (dd, 2H), 6.10 (d, 2H), 4.44-4.30 (m, 2H), 4.21 (t, 8H), 2.58-2.42 (m, 4H), 1.84-1.78 (m, 2H), 1.60-1.52 (m, 2H), 1.48-1.39 (m, 2H), 1.37-1.24 (m, 14H), 0.92-0.86 (m, 3H). $^{13}$C NMR (101 MHz, Acetonitrile-$d_3$) δ 156.3, 144.1, 143.5, 134.2, 117.9, 113.3, 91.1, 52.4, 48.3, 32.6, 30.4, 30.4, 30.3, 30.2, 30.1, 29.9, 27.3, 26.4, 23.4, 16.7, 14.4. HRMS (ESI): calcd. for $C_{31}H_{44}N_3^+$ $[M]^+$ calcd. 458.3535, found 458.3535.

Example 5

3,6-di(azetidin-1-yl)-10-(3-(trimethylsilyl)propyl) acridin-10-ium iodide (I-5)

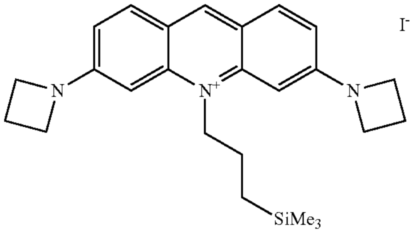 [SMILES: C[Si](C)(C)CCC[n+]1c2cc(N3CCC3)ccc2cc2ccc(N3CCC3)cc21 ; [I-]]

To a preheated suspension of 1 (25 mg, 0.086 mmol) in 4 ml of dichlorobenzene at 170° C. potassium phosphate (42 mg, 0.2 mmol) was added followed by the addition of 3-iodopropyl trimethylsilane (0.2 ml). Resulting mixture was stirred under reflux for 30 min. Then reaction mixture was evaporated, and residue was purified by flash chromatography on aluminum oxide using mixture of $CH_2Cl_2/C_2H_5OH$ (10:1) as eluent to yield 31 mg of 1-5 (67%).

$^1$H NMR (400 MHz, $CDCl_3$) δ 8.71 (s, 1H), 7.91 (d, 2H), 6.67 (dd, 2H), 6.22 (d, 2H), 4.70-4.56 (m, 2H), 4.29 (t, 8H), 2.62-2.55 (m, 4H), 1.99-1.74 (m, 2H), 0.91-0.73 (m, 2H), 0.03 (s, 9H). $^{13}$C NMR (101 MHz, $CDCl_3$) δ 155.2, 143.8, 142.6, 133.9, 117.3, 112.3, 90.4, 51.5, 50.8, 20.8, 16.1, 13.9, −1.7. HRMS (ESI): calcd. for $C_{25}H_{34}N_3^+$ $[M]^+$ calcd. 404.2517, found 404.2523.

Photo-physical properties of I-1-I-5 was measured in aqueous HEPES [4-(2-hydroxyethyl)piperazine-1-ethanesulfonic acid] buffer solution (20 mM, pH 7.4); NAO bromide was used as reference compound. Similar to NAO, derivatives I-1-I-5 have absorption maxima at 494-498 nm, and emission maxima at 528-529 nm (Table 1). However, surprisingly, the introduction of azetidinyl moieties instead of dimethylamino groups in NAO led to increase of Φ from 15.5% to 47.9% (I-3). Moreover, the trimethylsilylpropyl substituent in position 10 improved PLQY up to 60.7% (I-5). Notably, 10-methyl (I-1) and 10-methyl-$d_3$ (I-2) exhibit similar value of PLQY, 59.9% and 61.5%, correspondingly. The introduction of longer alkyl chains such as nonyl and dodecyl led to PLQY decrease.

TABLE 1

Photoluminescence properties of I-1-I-5

| Compound | $\lambda_{abs}$, nm | $\lambda_{em}$, nm | Φ, % |
|---|---|---|---|
| NAO | 498 | 528 | 15.5 |
| I-1 | 497 | 529 | 59.9 |
| I-2 | 497 | 529 | 61.5 |
| I-3 | 498 | 529 | 47.9 |
| I-4 | 494 | 528 | 16.1 |
| I-5 | 497 | 529 | 60.7 |

Mitochondrial membrane consists of 4 general phospholipids: phosphatidylcholine (PC), phosphatidylethanolamine (PE) and phosphatidylinositol (PI), and unique negatively charged phospholipid-cardiolipin (CL). I-5 interacts with CL/DOPC liposomes (3:1), this interaction can be observed as a fluorescence intensity drop from 65800 a.u. to 6600 a.u., similarly to NAO (from 13300 a.u. to 1260 a.u.).

I-5 is selective towards CL, since fluorescence intensity does not significantly decrease in the presence of DOPC liposomes without cardiolipin (7.7% drop), and I-5/CL optimal molar ratio was determined to be 2:1. Besides, NAO fluorescence intensity loss during interaction of DOPC was detected at 5.6% level. Notably, NAO fluorescence is not stable during experiments. It dropped by 15.5% in 30 minutes, however, fluorescence intensity of I-5 remaining the same.

I-5 was titrated with CL in 0.05-8 μM range and trustful linear regression curve ($R^2$=0.9944) was obtained (FIG. 1 represents linear regression curves for NAO and I-5 titration with cardiolipin). Consequently, we state that I-5 can be successfully used for qualitative and quantitative cardiolipin assay with superior fluorescence intensity and greater linear slope of the titration curve (−6259±250) compared to commercially available NAO (−1222±49).

Therefore, we claim water-soluble acridinium derivatives with improved fluorescence characteristics for selective CL detection.

Liposomes preparation. Vesicles were prepared by classic thin film method. Desired volume of stock solutions of DOPC (25 mg/ml, $CHCl_3$) and CL (5 mg/ml, EtOH) was completely evaporated on a vacuum line, and the lipid films were re-suspended in HEPES buffer (20 mM, pH 7.4) to acquire 100:300 μM CL/DOPC or 400 μM DOPC liposome 1$^{st}$ stock solutions. Obtained large multilamellar liposomes were sonicated in a bath-type sonicator at room temperature for 30 min following by extrusion through a 100 nm polycarbonate filter for 21 times. The quality of the resulting small unilamellar vesicles was monitored by dynamic light scattering (DLS) technique. These stock solutions were diluted 5-fold to acquire 2$^{nd}$ stock solutions that were used in the fluorometric experiments.

REFERENCES

[1] Paradies G, Paradies V, Ruggiero F M, Petrosillo G. Cells 2019; 8:728.

[2] McMillin J B, Dowhan W. Biochim Biophys Acta—Mol Cell Biol Lipids 2002; 1585:97-107.

[3] Han X, Yang J, Yang K, Zhongdan Z, Abendschein D R, Gross R W. Biochemistry 2007; 46:6417-28.

[4] Valianpour F, Wanders R J A, Overmars H, Vaz F M, Barth P G, Van Gennip A H. J Lipid Res 2003; 44:560-6.

[5] Pointer C B, Klegeris A. Cell Mol Neurobiol 2017; 37:1161-72.

[6] Paradies G, Paradies V, Ruggiero F M, Petrosillo G. Antioxidants Redox Signal 2014; 20:1925-53.

[7] Epand R M, Epand R F. BBA—Biomembr 2009; 1788: 289-94.

[8] Szeto H H. Br J Pharmacol 2014; 171:2029-50.

[9] El Khoury M, Swain J, Sautrey G, Zimmermann L, Van Der Smissen P, Décout J L, et al. Sci Rep 2017; 7:1-12.

[10] Sakamoto Y, Yano T, Hanada Y, Takeshita A, Inagaki F, Masuda S, et al. Eur J Pharmacol 2017; 800:48-56.

[11] Gorini S, De Angelis A, Berrino L, Malara N, Rosano G, Ferraro E. Oxid Med Cell Longev 2018; Nr. 7582730.

[12] Mileykovskaya E, Dowhan W, Birke R L, Zheng D, Lutterodt L, Haines T H. FEBS Lett 2001; 507:187-90.

[13] Kaewsuya P, Danielson N D, Ekhterae D. Anal Bioanal Chem 2007; 387:2775-82.

The invention claimed is:

1. A compound of Formula I:

I

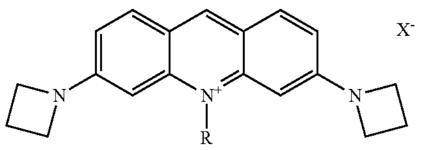

wherein

R represents $C_{1-6}$-alkylene-silyl($C_{1-3}$-alkyl)$_3$; and $X^-$ represents chloride, bromide, or iodide.

2. The compound of claim 1, wherein the compound has the structure:

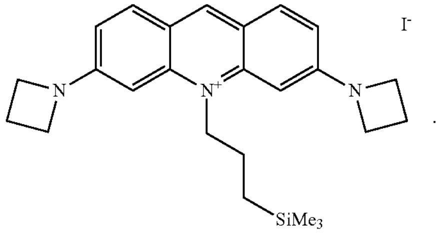 [SMILES: C[Si](C)(C)CCC[n+]1c2cc(N3CCC3)ccc2cc2ccc(N3CCC3)cc21 ; [I-]]

3. A process for the synthesis of a compound of Formula I:

I

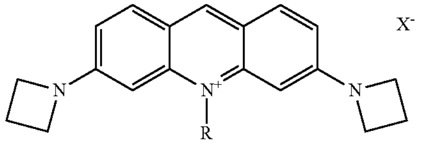

wherein:

R represents $C_{1-15}$ alkyl, $C_{1-3}$ deuterated alkyl, or $C_{1-6}$-alkylene-silyl($C_{1-3}$-alkyl)$_3$; and $X^-$ represents chloride, bromide, or iodide;

comprising reacting a compound 1:

1

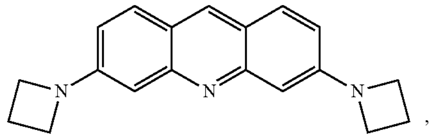

with $C_{1-12}$ alkyl halide, $C_{1-3}$ deuterated alkyl halide, or $C_{1-6}$-alkylene-silyl($C_{1-3}$-alkyl)$_3$ halide in the presence of potassium phosphate.

4. The compound of claim 1, wherein R is $C_{1-3}$-alkylene-silyl($C_{1-3}$-alkyl)$_3$.

5. The compound of claim 4, wherein R is $(CH_2)_3$—Si$(CH_3)_3$.

6. The compound of claim 5, wherein $X^-$ is iodide.

7. The process of claim 3, wherein R is $C_{1-12}$ alkyl, deuterated methyl, or $C_{1-3}$-alkylene-silyl($C_{1-3}$-alkyl)$_3$.

8. The process of claim 7, wherein R is $CH_3$, $CD_3$, $C_9H_{19}$, $C_{12}H_{25}$, or $(CH_2)_3$—Si$(CH_3)_3$.

9. The process of claim 8, wherein $X^-$ is iodide.

10. A method of detecting cardiolipin comprising contacting the compound of claim 1 with cardiolipin.

11. The method of claim 10, further comprising detecting a loss in fluorescence intensity.

* * * * *